(12) United States Patent
Netsch et al.

(10) Patent No.: US 8,369,927 B2
(45) Date of Patent: Feb. 5, 2013

(54) METHOD FOR CREATING A MODEL OF A STRUCTURE

(75) Inventors: Thomas Netsch, Eindhoven (NL); Daniel Bystrov, Hamburg (DE); Stewart Young, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1225 days.

(21) Appl. No.: 12/094,195

(22) PCT Filed: Nov. 8, 2006

(86) PCT No.: PCT/IB2006/054165
§ 371 (c)(1), (2), (4) Date: May 19, 2008

(87) PCT Pub. No.: WO2007/057816
PCT Pub. Date: May 24, 2007

(65) Prior Publication Data
US 2008/0281569 A1     Nov. 13, 2008

(30) Foreign Application Priority Data
Nov. 21, 2005  (EP) .................................... 05111008

(51) Int. Cl.
*A61B 5/05*      (2006.01)
*G06K 9/00*     (2006.01)
*G06K 9/34*     (2006.01)
*G06K 9/46*     (2006.01)

(52) U.S. Cl. ........ 600/408; 600/407; 382/128; 382/294; 382/190

(58) Field of Classification Search .................. 382/128, 382/294, 190; 600/408
See application file for complete search history.

(56) References Cited

U.S. PATENT DOCUMENTS
(Continued)

FOREIGN PATENT DOCUMENTS
EP  1465109 A2  10/2004
WO  2005010699 A2  2/2005
(Continued)

OTHER PUBLICATIONS

Fan, Y.; Guest, E.; Bowring, N.; , "Detection of mouse embryo atlas (MA) boundaries using a neural network," Parallel and Distributed Computing, Applications and Technologies, 2003. PDCAT'2003. Proceedings of the Fourth International Conference, vol., No., pp. 829-833, Aug. 27-29, 2003.*

Netsch, T., et al.; Grey value-based 3-D registration of functional MRI time-series: Comparison of interpolation order and similarity measure; 2000; Proc. of SPIE: Medical Imaging-Image Processing; vol. 3979:1148-1159.

(Continued)

*Primary Examiner* — Long V. Le
*Assistant Examiner* — Helene Bor

(57) ABSTRACT

A method for creating a model of a part of the anatomy from the scan data of several subjects is described. The method comprises the steps of collecting scan data; applying a feature detector to the scan data; converted the output of the feature detector into a common reference system; and accumulating the converted data to generate the model. It is therefore possible for the method to generate a model from the scan data of several subjects automatically. The method may also include an optional step of receiving user input to select which of the accumulated data should be included in the final model. This user input requires much less effort than manual contouring and is substantially independent of the number of subjects used to create the model.

20 Claims, 2 Drawing Sheets

U.S. PATENT DOCUMENTS

Figure 1:
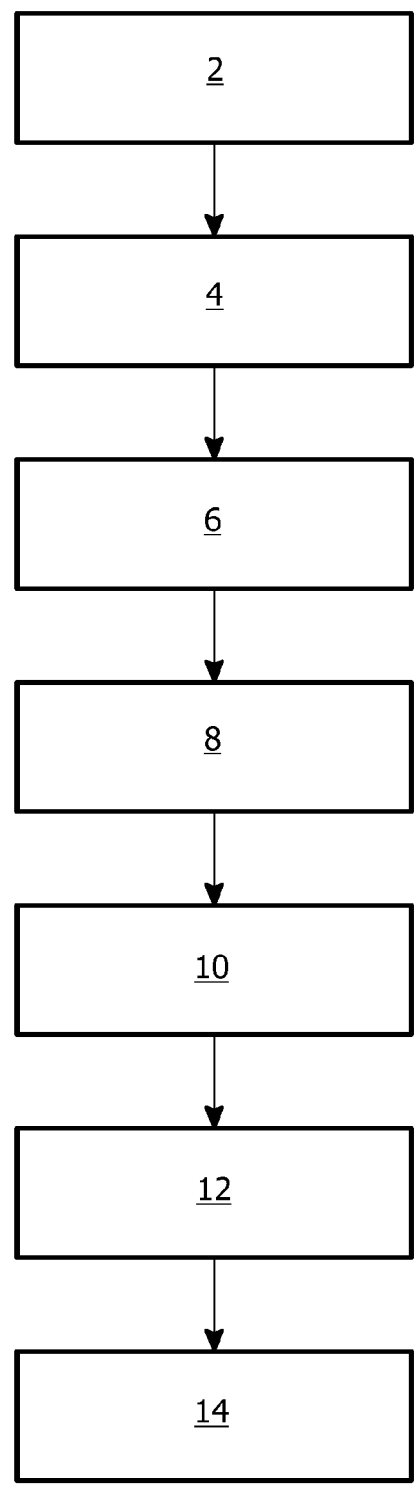

| | | | |
|---|---|---|---|
| 5,754,708 A * | 5/1998 | Hayashi et al. | 382/266 |
| 6,058,322 A * | 5/2000 | Nishikawa et al. | 600/408 |
| 6,597,801 B1 * | 7/2003 | Cham et al. | 382/103 |
| 7,409,108 B2 * | 8/2008 | Xu et al. | 382/294 |
| 2002/0057838 A1 * | 5/2002 | Steger | 382/197 |
| 2003/0139659 A1 * | 7/2003 | Dale et al. | 600/407 |
| 2004/0076317 A1 | 4/2004 | Roberts | |
| 2004/0101184 A1 | 5/2004 | Sivaramakrishna et al. | |

FOREIGN PATENT DOCUMENTS

| | | |
|---|---|---|
| WO | 2005023086 A2 | 3/2005 |

OTHER PUBLICATIONS

Perperidis, D., et al.; Building a 4D atlas of the cardiac anatomy and motion using MR imaging; 2004; Biomedical Imaging: Macro to Nano; pp. 412-415.

Shenton, M. E., et al.; Harvard Brain Atlas: A Teaching and Visualization Tool; 1995; Biomedical Visualization Proc.; pp. 10-17, 81.

Yan, Z-Z, et al.; Anatomical-Map System for CT Interpolation; 1992; IEEE Trans. on Pattern Recognition; vol. 2: pp. 246-250.

* cited by examiner

METHOD FOR CREATING A MODEL OF A STRUCTURE

The present invention relates to a method and apparatus for creating a model of a structure. In particular, the present invention relates to the creation of a model that is based on training data of several subjects and which relates to the structure of a part of the anatomy.

Various scanning techniques exist for producing medical images of a cross section of part of the body. These techniques include Magnetic Resonance Imaging (MRI), Computerized Tomography (CT) and Positron Emission Tomography (PET). The output data from these scanning techniques is typically in the form of a set of intensity values (often referred to as grey levels). In order for the data to be useful it is often necessary to interpret the output of a scan to build up a model of the area that has been scanned. This model can then be used, for example, to plan surgery or to plan a more detailed scan of a particular area.

One way of interpreting the output data of a scan to create a model is for a skilled operator to examine the images obtained and select the boundaries between anatomical features manually. This is known as contouring and can take some time, particularly when a three dimensional model is required. In order to create a three dimensional model it necessary for a large number of two dimensional scans of different cross sections to be contoured by the operator, these can then be combined into a three dimensional model.

In order to allow models for individual subjects to be created more quickly, methods that fully or partially automate the process of contouring have been proposed. For example, US 2004/0101184 A1 relates to an automated method for autocontouring organs and other anatomical structures in CT images. It discusses an edge-based method in which a point is determined to be in the interior of an organ and is then used as a starting point for detecting the edges of the organ. This technique is applied only to the creation of a model using data of a scan on a single subject, and requires some predetermined input of the general anatomical features of the scanned area (for example the bone configuration in a male's pelvic region) before the method can be used.

It is therefore an object of the invention to improve the efficiency of generating a model from scan data.

According to the present invention, there is provided a method for generating a model of a structure using scan data from a plurality of subjects, the method comprising:
collecting a set of scan data comprising scan data of the part of the anatomy for each of the plurality of individuals;
applying a feature detector to each item in the set of scan data to generate a set of feature data;
converting each item in the set of the feature data into a common reference system to generate a set of transformed data; and
accumulating each item in the set of transformed data to generate a model of the part of the anatomy representing a plurality of individuals.

Unlike US 2004/0101184 A1, the present invention uses data from a plurality of subjects to generate the model. The end result is a model that is representative of the variation of the structure across the data set on which the model is based. It is then possible to use the model in combination with scout data of an unknown subject, for example to plan detailed scan geometries. The method of the present invention can be used without any knowledge of the structure of the scanned area; the structural features are automatically generated.

The automated nature of the present invention allows it to be used to create a model that is based on data of an arbitrarily large number of subjects (for example more than fifty). Furthermore, the ease with which a model can be created enables a suite of models to be developed. This can be useful when it is desired to have a suite of models to reduce inter-population variation and improve the accuracy of the output model.

A further benefit of the present invention is that the model can be created using the same feature detection algorithm that will be used to identify the features in the data of an unknown subject. This improves the accuracy of matching the unknown data to the model.

Another advantage is that the model can be refined to incorporate new data with little effort due to its automated nature.

In medical imaging applications the structure may be an anatomical structure and each subject may be an individual patient.

The method of the present invention can be implemented by a computer program comprising code means for execution by a data processor. The computer program code may be embodied on a computer readable medium, for example a magnetic medium, such as a disk, an optical medium, such as a CD ROM, or a solid-state medium, such as flash memory. In that case it is possible for the computer program to be a retro-fit upgrade to an existing medical imaging apparatus.

The method may optionally include a step of displaying the model and user interaction, as defined by appended claim 2. This allows a user to select the most representative parts of the model for inclusion in a final model and allows the accuracy of the model to be improved. The user input required for this step is less than the previous method of manual contouring because the user simply has to select which contours generated by the automatic process should be included.

According to another aspect of the present invention, there is provided a medical imaging apparatus for generating a model of a structure using scan data from a plurality of subjects, the apparatus comprising:
a storage device for storing instructions executable by a data processing means and for storing a set of scan data of the part of the anatomy for each of the plurality of individuals; and
a data processor which can be configured by the instructions stored in the storage device to execute the steps of:
  collecting a set of scan data comprising scan data of the structure for each of the plurality of subjects;
  applying a feature detector to each item in the set of scan data to generate a set of feature data;
  converting each item in the set of the feature data into a common reference system to generate a set of transformed data; and
  accumulating each item in the set of transformed data to generate a model of the structure representing a plurality of subjects.

Figure 2:
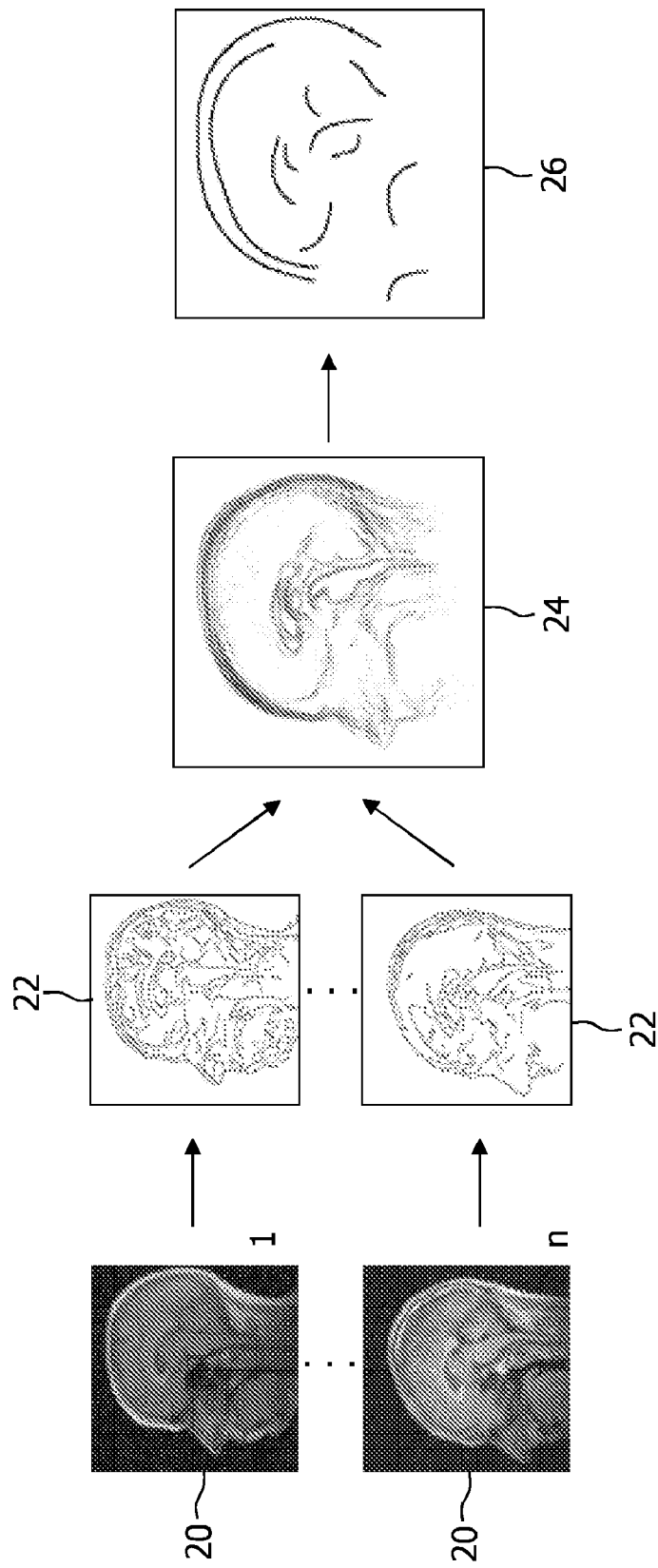

Embodiments of the present invention will now be discussed by way of example with reference to the accompanying drawings, in which:

FIG. 1 is a flow chart illustrating the method of a first embodiment of the present invention; and FIG. 2 is an example of the processed images at various stages in the method of FIG. 1.

A flow chart of a first embodiment of the present invention is shown in FIG. 1. A visual representation of a first embodiment of the present invention, showing representations of the processed images at each stage is depicted in FIG. 2. For simplicity of explanation this embodiment will be described in relation to the formation of a two dimensional model. However, the person skilled in the art will appreciate that it could equally apply to the formation of a three dimensional model.

In a first step 2, the scan data 20 on which the model is to be based is collected. This involves collecting data from several subjects that will be used to form the model (only two are depicted in FIG. 2 for simplicity). The scan data in this embodiment is grey level data representing the intensities obtained by an MR scan of the brain along the sagittal plane.

In a second step 4, a feature detector is applied to the raw data in order to extract information regarding the anatomical features contained in the scan. In this embodiment the feature detector is an edge detector. This generates a set of feature data 22. As can be seen in FIG. 2, the feature data produced at this stage contains a large number of possible locations of contours.

In a third step 6, the set of feature data 22 is converted into a common coordinate reference system. The common coordinate reference system optimizes the spatial correspondence of the features between images in the set of feature data. This step of converting the data is preferably implemented by an automatic algorithm, for example a rigid grey value based method. The individual images are also aligned in this step. It is preferred to register grey-value data. Alternatively, the feature data itself may be used directly.

In a fourth step 8, the set of transformed data is accumulated into a common space. In this embodiment the accumulation is carried out by building "edge pixel counting" histograms of each pixel in the transformed and aligned images output after the third step 6. For example, if a particular pixel contains a feature (an edge in this embodiment) in three of the transformed and aligned images, its histogram would have a value of three. In this way a probabilistic map 24 of the feature distribution across the images is built up. This map can be used directly as a model itself, by using the probabilistic margins when matching the model to new data.

However, as can be seen in FIG. 1, this data lacks some definition because of registration uncertainties between the transformed images and anatomical differences that were not captured during transformation of the data in the second step.

In order to develop a well-defined model, the method optionally includes a step of fitting manifolds to the pixels with the highest probabilities in the probabilistic map. For example, 2D spline curves or surfaces can be used.

This embodiment also includes optional steps of displaying 10 the initial model and receiving 12 user input. This allows the user to refine the final model by selecting those features which best represent the model, or those which are most pertinent to the intended application (using expert knowledge). Although some user interaction is optionally included in this embodiment, the effort required is far lower than manual contouring. The user is presented with a group of possible contours that need only be selected; there is no need for the user to trace the contour manually. Furthermore, the selection step need only be carried out once, no matter how many images are used in the creation of the model.

In a final step 14, the final model 26 is output. The final model 26 represents the variation of the features across the individual scan data used as the basis for the model in the first step 2.

The final model can be used in a variety of applications. For example, it can be used in combination with scout scan data of a patient to plan a detailed scan.

In an alternate embodiment, the transformation into a common coordinate reference system includes a step of user input. The user can indicate the location of predetermined "landmark" features within each image. It is important to note that this is not the same as a full manual contouring process: it has to be done only once and does not depend on the selection of contours. It is therefore possible to use this embodiment when the data is not suitable for rigid-or elastic-registration methods.

Further embodiments may make use of multi-dimensional features in the step of feature detection. For example directional information may be used.

Elastic registration methods may also be used in alternate embodiments to reduce anatomical variability.

It will be appreciated that the precise method of feature detection used and whether user interaction is required can depend on the particular application. For example using multi dimensional features in the feature detector may give better results in some circumstances than the edge detector of the first embodiment. Different feature detectors will result in different final models that are specific to a particular feature detector. This is an advantage as a better matching of unknown data to the model can then be achieved by processing the unknown data using the same feature detection that was used in creation of the model.

The method of the above embodiments can be used in a medical imaging apparatus, which in one embodiment is an MR apparatus. The MR apparatus comprises storage means, which may for example be volatile or non-volatile memory, magnetic storage such as a hard disk drive or optical storage such as a CD ROM. The storage means is used to store the instructions that are executed by a data processor to implement the method of the above embodiments. It is also possible for the storage means to store the scan data collected in the first step 2 of the method, and to store the final model, if required.

The method of the present invention may also be implemented by a computer program comprising code means that can be executed by a general purpose computer system comprising storage means and a data processor, as is generally known in the art.

The present invention can be applied to any form of medical imaging in which it is desired to create a model representative of a part of the anatomy using data from several individuals. This includes MRI, CT and PET scanning apparatus and well as other two dimensional and three dimensional medical imaging apparatus.

An advantage of the present invention is that it allows a model to be generated from scan data of multiple subjects automatically. No prior knowledge of the anatomical features is required before the model is generated and user input is reduced, or even not required at all. This is especially useful when it is desired to automatically update models with new data, or to generate models based on scan data of a large number of individuals.

The features of the individual embodiments may be combined. "Comprising" is used throughout this application to indicate an inclusive definition and does not preclude the presence of other items.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for generating a model of an anatomical structure using scan data from a plurality of subjects, the method comprising:

collecting a set of scan data comprising scan data of the anatomical structure for each of the plurality of subjects;

applying an edge detector to the set of scan data for each of the plurality of subjects to generate sets of edges;

converting the sets of the edges into a common reference system;

accumulating the sets of the edges in the common reference system to form a probability map;

displaying the probability map;

fitting curves or surfaces to the probability map to select representative edge portions to define the model of the anatomical structure.

2. The method according to claim 1, further comprising: refining the model with additional edges.

3. The method according to claim 1, wherein the step of accumulating includes determining a histogram indicative of a probability each voxel defines a portion of one of the set of edges.

4. The method according to claim 1, wherein the step of converting into the common reference system comprises using a registration algorithm.

5. The method according to claim 4, wherein the registration algorithm is a rigid grey value based registration algorithm.

6. The method according to claim 1, wherein the step of converting into the common reference system comprises user input to establish the set of edges.

7. The method according to claim 1, wherein the step of accumulating comprises voxel edge counting to determine locations of the set of edges.

8. A non-transitory computer-readable medium carrying computer code that, when executed by a data processor, instructs the data processor to perform the method of claim 1.

9. The method according to claim 3, wherein the curves or surfaces are fit to voxels with a highest probability of being the edges.

10. A medical imaging apparatus for generating a model of an anatomical structure using scan data from a plurality of subjects, the apparatus comprising:

a storage device which stores instructions executable by a data processor and which stores a set of scan data of the anatomical structure for each of the subjects; and a data processor configured by the instructions stored in the storage device to execute the steps of:

collecting a set of scan data comprising scan data of the anatomical structure of each of the plurality of subjects;

applying a feature detector to each set of scan data to generate a set of feature data;

converting each set of the feature data into a common reference system and forming a probability map;

fitting curves or surfaces to corresponding structural features in said sets of feature data of the probability map to define the model of the anatomical structure.

11. The medical imaging apparatus according to claim 10, further comprising:

a display device for displaying an image of the sets of feature data in the common reference system; and an input device for receiving user input;

wherein the data processor is further configured by the instructions stored in the storage device to receive user input that indicates parts of the displayed image to be incorporated in the model.

12. The imaging apparatus according to claim 10, wherein the probability map is formed by determining a probability that each voxel represents the corresponding structural feature and the curves or surfaces are fit to the voxels with a highest probability of being the corresponding structural feature.

13. The imaging apparatus according to claim 10, wherein to apply the feature detector, the data processor is further configured to:

apply an edge detector to each set of the scan data to generate edge contours, the sets of feature data including the edge contours.

14. The imaging apparatus according to claim 13, wherein the probability map is formed by determining a probability that each voxel represents a portion of the edge contour and the curves or surfaces are fit to the voxels with a highest probability of being the portion of the edge contour to define the model of the anatomical structure.

15. The imaging apparatus according to claim 14, wherein to convert to the common reference system, the data processor is further configured to:

apply a rigid registration algorithm to the edge contours.

16. The imaging apparatus according to claim 14, wherein determining the probability includes generating a histogram.

17. The imaging apparatus according to claim 14, wherein the data processor is further configured to:

receive a scout scan; and apply the model to the scout scan to generate a planning image in the common reference system.

18. A medical imaging apparatus for generating a model of an anatomical structure using scan data from a plurality of subjects, the apparatus comprising:

at least one processor programmed to:

receive a set of the scan data of the anatomical structure from each of the plurality of subjects;

apply a feature detection routine to sets of scan data to generate sets of feature data;

convert the sets of feature data into a common reference system;

determine from the sets of the feature data in the common reference system a probability that each voxel of the common reference system represents a common characteristic of the feature data;

fit curves or surfaces to the voxels with a highest probability to define the model.

19. The imaging apparatus according to claim 18, wherein determining the probability includes determining a histogram.

20. The imaging apparatus according to claim 18, wherein the feature detection routine determines edges.

* * * * *